United States Patent
Chen (12)

(10) Patent No.: US 9,303,281 B2
(45) Date of Patent: Apr. 5, 2016

(54) COMPOSITIONS FOR DETECTING FOODSTUFF SPOILAGE MICROORGANISMS

(75) Inventor: Caifu Chen, Palo Alto, CA (US)

(73) Assignee: Pall Corporation, Port Washington, NY (US)

( * ) Notice: Subject to any disclaimer, the term of this patent is extended or adjusted under 35 U.S.C. 154(b) by 838 days.

(21) Appl. No.: 13/555,399

(22) Filed: Jul. 23, 2012

(65) Prior Publication Data

US 2014/0024543 A1 Jan. 23, 2014

(51) Int. Cl.
| | | |
|---|---|---|
| *C12Q 1/68* | (2006.01) | |
| *C12Q 1/04* | (2006.01) | |
| *C12Q 1/26* | (2006.01) | |
| *C12Q 1/58* | (2006.01) | |
| *C12Q 1/66* | (2006.01) | |

(52) U.S. Cl.
CPC .. *C12Q 1/04* (2013.01); *C12Q 1/26* (2013.01); *C12Q 1/58* (2013.01); *C12Q 1/66* (2013.01); *C12Q 1/689* (2013.01)

(58) Field of Classification Search
None
See application file for complete search history.

(56) References Cited

U.S. PATENT DOCUMENTS

| | | | |
|---|---|---|---|
| 5,484,909 A | 1/1996 | Nietupski et al. | |
| 5,705,339 A | 1/1998 | Nietupski et al. | |
| 6,103,468 A | 8/2000 | Russell et al. | |
| 6,821,771 B2 | 11/2004 | Festoc | |
| 7,014,994 B1 | 3/2006 | Barany et al. | |
| 7,183,085 B1 | 2/2007 | Fandke et al. | |
| 7,553,956 B2 | 6/2009 | Fujii | |
| 8,017,359 B2 | 9/2011 | Brodmann et al. | |
| 2004/0248115 A1 | 12/2004 | Fujii | |
| 2005/0272062 A1 | 12/2005 | Kodama et al. | |
| 2008/0026368 A1 | 1/2008 | Snaidr et al. | |
| 2009/0142750 A1 | 6/2009 | Nakakita et al. | |

FOREIGN PATENT DOCUMENTS

| | | |
|---|---|---|
| EP | 0 890 650 A2 | 1/1999 |
| EP | 1 106 688 A1 | 6/2001 |
| EP | 1 609 871 A1 | 12/2005 |
| EP | 1 721 975 A1 | 11/2006 |
| EP | 1 724 345 A1 | 11/2006 |
| FR | 2 844 522 A1 | 3/2004 |
| JP | 10210980 A | 8/1998 |
| JP | 2005006556 A | 1/2005 |
| JP | 2007-505638 A | 3/2007 |
| JP | 2007-259730 A | 10/2007 |
| JP | 2008-263971 A | 11/2008 |
| JP | 2010-081935 A | 4/2010 |
| SG | 111927 A1 | 6/2005 |
| WO | WO 2004/106547 A2 | 12/2004 |
| WO | WO 2009/039549 A2 | 4/2009 |

OTHER PUBLICATIONS

Notice of Reasons for Rejection, Japanese Application No. P2013-152725 dated Nov. 18, 2014.
Suzuki, K. et al., "Genetic characterization and specific detection of beer-spoilage *Lactobacillus* sp. LA2 and related strains," *J. Applied Microbiology*, 96, 677-83 (2003).
Suzuki, K. et al., "*Lactobacillus paracollinoides* sp. nov,, isolated from brewery environments" *Int. J. of System. and Evol. Microbiol.*, 54, 115-17 (2004).
Search Report, European Application No. 13172688.7, mailed Dec. 10, 2013.
Search Report, Singapore Application No. 201304698-2, mailed Dec. 6, 2013.
Hanna, S.E. et al., "Real-time polymerase chain reaction for the food microbiologist: technologies, applications, and limitations," *Journal of Food Science*, 70(3), R49-R53 (2005).
Scheu, P.M. et al., "Detection of pathogenic and spoilage microorganisms in food with the polymerase chain reaction," *Food Microbiology*, 15, 13-31 (1998).
Weber, D.G. et al., "Oligonucleotide microarrays for the detection and identification of viable beer spoilage bacteria," *Journal of Applied Microbiology*, 105(4), 951-962 (2008).
Chiang, Y.C. et al., "Multiplex PCR and a chromogenic DNA macroarray for the detection of listeria monocytogens, Staphylococcus aureus, Streptococcus agalactiae, enterobacter sakazakii, Escherichia coli O157:H7, vibrio parahaemolyticus, Salmonella spp. And pseudomonas fluorescens in milk and meat samples," *Journal of Microbiological Methods*, 88(1), 110-116 (2011).

*Primary Examiner* — Jim Ketter
(74) *Attorney, Agent, or Firm* — Leydig, Voit & Mayer, Ltd.

(57) ABSTRACT

The invention provides nucleic acids, collections of nucleic acids, assay kits, and methods for the sensitive and specific detection of microorganisms in a foodstuff. The nucleic acid consists of a nucleotide sequence selected from the group consisting of SEQ ID NOs: 1-45.

7 Claims, No Drawings

COMPOSITIONS FOR DETECTING FOODSTUFF SPOILAGE MICROORGANISMS

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,781 Byte ASCII (Text) file named "710675SequenceListing," dated Jul. 20, 2012.

BACKGROUND OF THE INVENTION

Microorganisms (e.g., bacteria) may cause the spoilage of foodstuffs (e.g., beer) during or after manufacture. Some microorganisms may cause foodstuff spoilage and any one or more of several undesirable effects such as, for example, unpleasant odor, unpleasant taste, and rendering the foodstuff unsafe for consumption. Failure to accurately and rapidly detect the presence of foodstuff-spoiling microorganisms may increase the risk of food spoilage. Obstacles to the rapid and accurate detection of the microorganisms that cause the spoilage of foodstuffs may include, for example, the lengthy duration of the traditional microbiology methods used to detect the microorganisms. These traditional methods may take an average of 7-14 days to complete. Another obstacle to accurate detection may include, for example, the similarity of the genomic sequences of some foodstuff-spoiling microorganisms as compared to that of non-foodstuff-spoiling microorganisms.

Accordingly, there is a need for improved compositions and methods for detecting microorganisms that cause the spoilage of foodstuffs.

BRIEF SUMMARY OF THE INVENTION

An embodiment of the invention provides a nucleic acid consisting of a nucleotide sequence selected from the group consisting of SEQ ID NOs: 1-45.

Another embodiment of the invention provides a collection of nucleic acids comprising two or more nucleic acids, wherein the two or more nucleic acids each consist of a nucleotide sequence selected from the group consisting of SEQ ID NOs: 1-45.

Another embodiment of the invention provides an assay kit comprising a collection of nucleic acids, wherein the collection is selected from the group consisting of (a) SEQ ID NOs: 1-3; (b) SEQ ID NOs: 4-6; (c) SEQ ID NOs: 7-9; (d) SEQ ID NOs: 10-12; (e) SEQ ID NOs: 13-15; (f) SEQ ID NOs: 16-18; (g) SEQ ID NOs: 19-21; (h) SEQ ID NOs: 22, 24, and 27; (i) SEQ ID NOs: 22, 25, and 27; (j) SEQ ID NOs: 23, 26, and 27; (k) SEQ ID NOs: 28-30; (l) SEQ ID NOs: 31-33; (m) SEQ ID NOs: 34-36; (n) SEQ ID NOs: 37-39; (o) SEQ ID NOs: 40-42; and (p) SEQ ID NOs: 43-45.

Still another embodiment of the invention provides a method of detecting the presence of one or more microorganisms in a foodstuff, the method comprising: (a) obtaining at least one test sample comprising isolated microorganism nucleic acid from foodstuff; (b) contacting the inventive nucleic acid, collection of nucleic acids, or support including at least one inventive nucleic acid with the at least one test sample under conditions allowing for a complex to form between the inventive nucleic acid and the microorganism nucleic acid; (c) detecting the complex; and, optionally, (d) comparing an amount of complex in the at least one test sample with an amount of complex from a negative sample that lacks microorganism nucleic acid, wherein an increased amount of complex from the at least one test sample is indicative of the presence of one or more microorganisms.

DETAILED DESCRIPTION OF THE INVENTION

An embodiment of the invention provides a nucleic acid consisting of a nucleotide sequence selected from the group consisting of SEQ ID NOs: 1-45. In an embodiment, the nucleic acid is isolated or purified. The inventive nucleic acids provide forward primers, reverse primers, and probes which may, advantageously, specifically hybridize with a microorganism nucleic acid for detection of the presence of one or more microorganisms in a foodstuff. In some embodiments, the primers and probes specifically hybridize with the nucleic acid of a specific genus of microorganisms. In an especially preferred embodiment, the primers and probes specifically hybridize with the nucleic acid of a specific species of microorganisms.

The inventive nucleic acids may be used to detect the presence of one or more microorganisms that cause foodstuff spoilage in a sample of foodstuff. In an embodiment of the invention, the inventive nucleic acids may specifically detect one or more microorganisms of one or more genera selected from the group consisting of *Pediococcus*, *Lactobacillus*, *Pectinatus*, and *Megasphaera*. Exemplary species of microorganisms specifically detectable by the inventive nucleic acids are set forth in Table 1.

TABLE 1

| Assay Kit No. | Species | Component | Sequence | SEQ ID NOs: |
|---|---|---|---|---|
| 1. | *Lactobacillus collinoides* | forward primer | ACGAACGCATCCCGTTAAA | 1 |
| | | reverse primer | GGACCAGTTCGCCACTCATCC | 2 |
| | *L. paracollinoides* | probe | CAAGTGCTTGCACGGATTTTAACATTG | 3 |
| 2. | Inhibition Control | forward primer | CTTGCAAATCGTTCTTTGGG | 4 |
| | | reverse primer | TAGCGGTACGACTGTCTTGG | 5 |
| | | probe | TCAAACCCTAACCTCAGCTCCAGC | 6 |
| 3. | *L. backii* | forward primer | TCCAAGTCGAACGCACAGATA | 7 |
| | | reverse primer | GGGAAATGTTATCCCCCACTTTT | 8 |
| | | probe | AGTGGCGGACGGGTGAGTAACACG | 9 |
| 4. | *L. brevis* | forward primer | AACGAGCTTCCGTTGAATGAC | 10 |
| | | reverse primer | CGGCCTGCTTCTGGGCAGA | 11 |
| | | probe | TGCTTGCACTGATTTCAACAATGAAGC | 12 |

TABLE 1-continued

| Assay Kit No. | Species | Component | Sequence | SEQ ID NOs: |
|---|---|---|---|---|
| 5. | Pectinatus (P. cerevisiiphilus, P. frisingensis, P. haikarae & P. portalensis) | forward primer<br>reverse primer<br>probe | TCAAGTTCTGTTGCAGGGGA<br>ACCGGACAACGCTTGCCG<br>TGAATGACGGTACCCTGTTAGAAAGCC | 13<br>14<br>15 |
| 6. | L. lindneri | forward primer<br>reverse primer<br>probe | CGTCGAACGAGGTCTCCTAAC<br>GCCTTCCAGGTGTTATCCCCTT<br>AGTGGCGAACTGGTGAGTAACACGT | 16<br>17<br>18 |
| 7. | Megasphaera (M. cerevisiae, M. elsdenii) | forward primer<br>reverse primer<br>probe | CGCGTGACGGTACCGTAAG<br>GGAGCCCCGCACTTTTAAGAC<br>TACCGTAAGAGAAAGCCACGGCTAA | 19<br>20<br>21 |
| 8. | Pediococcus (P. damnosus, P. inopinatus, P. claussenii) | forward primer damnosus and inopinatus<br>forward primer claussenii<br>reverse primer damnosus<br>reverse primer inopinatus<br>reverse primer claussenii<br>probe | CGTAGAGATGCTTGCATCGAA<br>GGCTTGCACGGATAGATGATT<br>CCAACCATGCGGITCATTTTA<br>CCAAACCATGCGGTTTACTTTA<br>CCAACCATGCGGTTTTCTTTA<br>AGTGGCGAACGGGTGAGTAACACG | 22<br>23<br>24<br>25<br>26<br>27 |
| 9. | L. casei | forward primer<br>reverse primer<br>probe | TGGCTTGCACTGAGATTCGA<br>CCACCATGCGGTTCTTGGAT<br>AGTGGCGGACGGGTGAGTAACACG | 28<br>29<br>30 |
| 10. | L. coryniformis | forward primer<br>reverse primer<br>probe | CAACGCACTGACGTCGACC<br>AGCCAAAGGCCGTCTTTTACATT<br>AGTGGCGGACGGGTGAGTAACACG | 31<br>32<br>33 |
| 11. | L. parabuchneri (L. frigidus) | forward primer<br>reverse primer<br>probe | CCTGTTGAGTGCTTGCATTTAACTG<br>GGCCAAGTGTTATCCCCTACTTCAA<br>AGTGGCGAACTGGTGAGTAACACGT | 34<br>35<br>36 |
| 12. | L. perolens | forward primer<br>reverse primer<br>probe | CCAGGTGCTTGCATCACCA<br>TTTCCAAATGTTATCCCCTGCTG<br>AGTGGCGGACGGGTGAGTAACACG | 37<br>38<br>39 |
| 13. | L. plantarum | forward primer<br>reverse primer<br>probe | TGAAGTCGAACGAACTCTGGTA<br>GCCCGAAGCCATCTTTCAAACTC<br>AGTGGCGAACTGGTGAGTAACACGT | 40<br>41<br>42 |
| 14. | L. rossiae | forward primer<br>reverse primer<br>probe | ACACGGTGCTTGCACCAGA<br>GGCAAATGTTATCCCCCACTTTA<br>AGTGGCGAACGGGTGAGTAACACG | 43<br>44<br>45 |

The inventive nucleic acids can specifically detect any type of microorganism nucleic acid. In an embodiment of the invention, the microorganism nucleic acid is DNA. In still another embodiment, the inventive nucleic acid is a nucleic acid consisting of a nucleotide sequence that is complementary to any of SEQ ID NOs: 1-45. The nucleic acid that is complementary to any of SEQ ID NOs: 1-45 may detect microorganism RNA.

In an embodiment, the inventive nucleic acid further comprises a detectable label. The label may be any label suitable for detecting hybridization, e.g., a complex, of the inventive nucleic acid with microorganism nucleic acid. Exemplary detectable labels may include any one or more of radioactive labels, non-radioactive labels, fluorescent labels, and chemiluminescent labels.

Another embodiment of the invention provides a collection of nucleic acids comprising two or more nucleic acids, wherein the two or more nucleic acids each consist of a nucleotide sequence selected from the group consisting of SEQ ID NOs: 1-45. In an embodiment of the invention, the collection may comprise or further comprise a nucleotide sequence complementary to a nucleotide sequence selected from the group consisting of SEQ ID NOs: 1-45. The collection may comprise any suitable number of inventive nucleic acids. For example, the collection may comprise from about 2 to about 45 or more nucleic acids, from about 10 or less to about 40 or more nucleic acids, or from about 20 or less to about 30 or more nucleic acids. In this regard, the collection may comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, or 45 or more nucleic acids. Although the two or more nucleic acids of the collection may be identical to one another, in a preferred embodiment, the two or more nucleic acids are different from each other. Accordingly, the two or more different nucleic acids may, advantageously, hybridize with two or more different microorganism nucleic acids and, therefore, detect the presence of two or more different microorganisms in a foodstuff.

An embodiment of the invention provides an assay kit comprising a collection of nucleic acids for the specific detection of one or more species of one or more microorganisms. The collection of nucleic acids of the assay kit may include at least one primer and a probe, preferably at least one forward primer, at least one reverse primer, and at least one probe. In an embodiment, the assay kit is selected from the group consisting of assay kit numbers 1-14 of Table 1. Preferably, the collection of nucleic acids of the assay kit is selected from the group consisting of (a) SEQ ID NOs: 1-3; (b) SEQ ID NOs: 4-6; (c) SEQ ID NOs: 7-9; (d) SEQ ID NOs: 10-12; (e) SEQ ID NOs: 13-15; (f) SEQ ID NOs: 16-18; (g) SEQ ID NOs: 19-21; (h) SEQ ID NOs: 22, 24, and 27; (i) SEQ ID NOs: 22, 25, and 27; (j) SEQ ID NOs: 23, 26, and 27; (k) SEQ ID NOs: 28-30; (l) SEQ ID NOs: 31-33; (m) SEQ ID NOs: 34-36; (n) SEQ ID NOs: 37-39; (o) SEQ ID NOs: 40-42; and (p) SEQ ID NOs: 43-45. In an embodiment, the assay kit may include sequences that are complementary to any one or more of SEQ ID NOs: 1-45.

By "nucleotide sequence" or "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the inventive nucleic acid does not comprise any insertions, deletions, inversions, and/or substitutions. However, it may be suitable in some instances, as discussed herein, for the nucleic acid to comprise one or more insertions, deletions, inversions, and/or substitutions.

The inventive nucleic acids can be constructed based on chemical synthesis and/or enzymatic ligation reactions using procedures known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, 3-(3-amino-3-N-2-carboxypropyl)uracil, and 2,6-diaminopurine. Alternatively, one or more of the nucleic acids of the invention can be purchased from companies, such as Macromolecular Resources (Fort Collins, Colo.) and Synthegen (Houston, Tex.).

An embodiment of the invention provides a support comprising the inventive nucleic acid, collection of nucleic acids, or collection of nucleic acids of the assay kit immobilized on the support. Another embodiment of the invention provides a support comprising the sample to be tested immobilized on the support, and the inventive nucleic acid is applied to the support. The support may be any support suitable for immobilizing the inventive nucleic acids. Exemplary supports are described in U.S. Pat. No. 6,821,771, which is incorporated herein by reference in its entirety. Other exemplary supports include GENEDISC plates available from Pall Corporation, Port Washington, N.Y., USA.

The support may further comprise a detectable label. The label may be any label suitable for detecting a complex of the inventive nucleic acid with microorganism nucleic acid. Exemplary detectable labels may include any one or more of radioactive labels, non-radioactive labels, fluorescent labels, and chemiluminescent labels.

Still another embodiment of the invention provides a method of detecting the presence of one or more microorganisms in a foodstuff, the method comprising: (a) obtaining at least one test sample comprising isolated microorganism nucleic acid from foodstuff; (b) contacting the inventive nucleic acid, collection of nucleic acids, collection of nucleic acids of the assay kit, or support including at least one nucleic acid with the at least one test sample under conditions allowing for a complex to form between the inventive nucleic acid and the microorganism nucleic acid; (c) detecting the complex; and (d) comparing an amount of complex in the at least one test sample with an amount of complex from a negative sample that lacks microorganism nucleic acid, wherein an increased amount of complex from the at least one test sample is indicative of the presence of one or more microorganisms.

The method may comprise obtaining a sample of the foodstuff to be tested and culturing microorganisms in the sample in any suitable manner. For example, when the foodstuff is beer, the sample may be any one or more of clear beer, non-filtered beer, processed beer, fermented beer, or other turbid beer.

The method may comprise culturing the microorganisms in any suitable culturing medium as is known in the art. The culturing medium may be selected depending on the nature of the foodstuff and microorganism to be tested. Exemplary culturing media may include enrichment broth such as, for example, MRS enrichment broth available from AES CHEMUNEX, Inc., Cranbury, N.J., USA; and NBB-C enrichment broth available from VWR International, West Chester, Pa., USA.

The microorganisms may be cultured at any suitable temperature and for any suitable duration as is known in the art. The culturing temperature and duration may be selected depending on the nature of the foodstuff and microorganism to be tested. For example, the microorganisms may be cultured at a temperature of about 20° C. to about 40° C., preferably from about 22° C. to about 28° C. The microorganisms may be cultured for about 1 day to about 14 days, preferably from about 2 days to about 7 days.

The method may comprise extracting nucleic acid from the microorganisms in any suitable manner as is known in the art. The nucleic acid may be RNA and/or DNA. The protocol for extracting nucleic acid may be selected depending on the nature of the foodstuff, microorganism, and nucleic acid to be tested as is known in the art. Preferably, the nucleic acid is extracted in any manner that lyses Gram positive and Gram negative bacteria and which recovers a testable amount of DNA without using polymerase chain reaction (PCR) inhibitors. The nucleic acid extraction may be carried out using any of a variety of commercially available nucleic acid extraction kits according to the manufacturer's instructions. Exemplary DNA extraction kits may include, for example, PEFOOD kit (available from Pall Corporation, Port Washington, N.Y., USA).

The method comprises contacting the inventive nucleic acid, collection of nucleic acids, collection of nucleic acids of the assay kit, or support with the at least one test sample under conditions allowing for a complex to form between the inventive nucleic acid and the microorganism nucleic acid. In this regard, the method comprises contacting the sample of extracted nucleic acid with the inventive nucleic acid under conditions which allow the inventive nucleic acid to specifically hybridize with microorganism nucleic acid as is known in the art. The method may comprise amplifying the inventive nucleic acid and the microorganism nucleic acid using any suitable type of PCR as is known in the art.

The method comprises detecting the complex. The complex may be detected using, for example, a radioactive label or a dye as is known in the art. In a preferred embodiment, the method comprises measuring light emitted from a fluorescent dye using, e.g., a laser. Detecting the complex may further comprise measuring the amount of complex formed.

In an embodiment, the method optionally comprises comparing an amount of complex in the at least one test sample with an amount of complex from a negative sample that lacks microorganism nucleic acid, wherein an increased amount of complex from the at least one test sample is indicative of the presence of one or more microorganisms. In this regard, the sample is negative for the foodstuff-spoiling microorganism if the amount of complex detected in the sample is no more than the amount of complex that is detected in a negative sample that is known to lack the microorganism nucleic acid. The sample is positive for the foodstuff-spoiling microorganism if the amount of complex detected in the sample is more than the amount of complex that is detected in a negative sample that is known to lack the microorganism nucleic acid.

The method may, advantageously, comprise testing for the presence of microorganisms in more than one different foodstuff sample simultaneously. In this regard, the at least one test sample may be two or more different samples tested sequentially or simultaneously, i.e., 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more samples sequentially or simultaneously.

The method may comprise detecting the presence of any one or more microorganisms that causes spoilage of foodstuff. In an embodiment of the invention, the method comprises detecting the presence of one or more microorganisms of one or more genera selected from the group consisting of *Pediococcus, Lactobacillus, Pectinatus*, and *Megasphaera*. In a preferred embodiment, the method comprises detecting the presence of one or more species of microorganisms selected from the group consisting of *Pediococcus damnosus, Pediococcus inopinatus, Pediococcus claussenii, Lactobacillus backii, Lactobacillus brevis, Lactobacillus casei, Lactobacillus coryniformis, Lactobacillus collinoides, Lactobacillus lindneri, Lactobacillus rossiae, Lactobacillus parabuchneri, Lactobacillus paracollinoides, Lactobacillus perolens, Lactobacillus plantarum, Pectinatus cerevisiiphilus, Pectinatus frisingensis, Pectinatus haikarae, Pectinatus portalensis, Megasphaera cerevisiae*, and *Megasphaera elsdenii*.

The method may comprise detecting microorganisms in any foodstuff. The foodstuff may be, for example, any one or more of dairy products; fats, oils, and fat emulsions; edible ices (including, e.g., sherbet and sorbet); fruits and vegetables (including, e.g., mushrooms and fungi, roots and tubers, pulses and legumes, and aloe vera); seaweeds; nuts and seeds; confectioneries; cereals and cereal products; baked goods (e.g., bread); meat and meat products (including, e.g., poultry and game); fish and fish products (including mollusks, crustaceans, and echinoderms); eggs and egg products; sweeteners, including, e.g., honey; salts, spices, soups, sauces, salads, protein products; foodstuffs intended for particular nutritional uses; and beverages (e.g., beer and wine). In a preferred embodiment, the foodstuff is beer.

The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, 90% or can be 100%.

The following examples further illustrate the invention but, of course, should not be construed as in any way limiting its scope.

EXAMPLE 1

This example demonstrates the quantitative detection of *L. casei* using the inventive nucleic acids.

Genomic DNA is isolated from *L. casei* (American Type Culture Collection (ATCC) strain reference E-011808) using a DNA Extraction Kit (available from Pall Corporation, Port Washington, N.Y., USA). Bacterial DNA is diluted with 10 mM Tris-pH 8.3 to a concentration of 83 pg/µL. Tris-pH 8.3 buffer (10 mM) is used as a no target control (NTC).

An *L. casei* assay kit (including a forward primer (SEQ ID NO: 28), a reverse primer (SEQ ID NO: 29), and a probe (SEQ ID NO: 30)) is used to test DNA from *L. casei* at 0 (NTC), 10, 1,000 or 100,000 copies per PCR well. The probe is labeled with 6-FAM fluorescent dye at 5' and BHQ1 quencher at 3' or ROX fluorescent dye at 5' and BHQ2 quencher at 3'.

A GENEDISC plate (available from Pall Corporation, Port Washington, N.Y., USA) is prepared according the manufacturer's instructions.

A quantitative (q) PCR mix kit ("Master Mix") (included in the GENEDISC detection kit, available from Pall Corporation, Port Washington, N.Y., USA) is prepared including SEQ ID NOs: 28-30. The barcode located on the GENEDISC plate and the barcode on the identification card contained in the Master Mix bag are scanned using the barcode reader fitted to the GENEDISC cycler (available from Pall Corporation, Port Washington, N.Y., USA). The sample names are entered according to the manufacturer's instructions for the GENEDISC cycler. Six 1.5 mL microtubes corresponding to each of the GENEDISC plate sectors are labeled. The Master Mix is vortexed for 2 seconds, then briefly centrifuged for 2 seconds. Master Mix (37 µL) is added to each microtube. The microtubes are closed. The DNA samples are centrifuged in a bench centrifuge for 15 seconds.

A DNA sample (37 µL) is transferred to the corresponding microtube containing the Master Mix using a pipette. The tube is closed to prevent cross-contamination. The tubes are gently mixed for 2 seconds and then centrifuged for 2 seconds using a mini centrifuge. These steps are repeated for each of the other 5 samples. 72 µL from each microtube is added to the appropriate GENEDISC plate sector.

The GENEDISC plates are loaded. The filling cap is placed on the top of the GENEDISC plate, the cap is gently pressed to ensure that there is no leakage and the vacuum is started. When the GENEDISC cycler indicates that the vacuuming is 90% complete, the GENEDISC plate is tapped to remove any residual bubbles. The cap is removed after the vacuum is released. Mineral oil (4 drops) are loaded into each GENE-DISC plate sector. The filling cap is placed on the GENE-DISC plate and the vacuum is started. The cap is removed at the end of the vacuum cycle and is cleaned by wiping with 70% ethanol. The wells are examined to ensure that there are no partially or unevenly filled wells present that may cause the assay kit to be aborted.

The filling cap is replaced in the designated location. The GENEDISC plate is carefully inserted into the GENEDISC cycler and the lid of the GENEDISC cycler is closed. The PCR is run using the thermal cycling condition. The thermal cycling condition includes tour temperatures 113° C., 107° C., 57° C., and 63° C. The cycling time is 70 seconds per cycle for 45 cycles. At the end of the PCR, the GENEDISC place is removed and discarded.

The data are analyzed. The *L. casei* assay (SEQ ID NOs: 28-30) quantitatively detects *L. casei* target DNA at 10, 1,000 and 100,000 copies per PCR well. There is no signal in the absence of target or with the "no template" control (NTC). NTC measures non-specific signal in the absence of target molecules. The inhibition control provides a positive PCR signal and measures the degree of PCR inhibition in the presence of sample or contaminant(s) in the sample.

EXAMPLE 2

This example demonstrates the specificity of the inventive nucleic acids.

Genomic DNA is isolated from 13 beer spoiling bacteria (Table 2) and diluted as described in Example 1. Tris-pH 8.3 buffer (10 mM) is used as a no target control (NTC). All bacterial strains are obtained from the American Type Culture Collection (ATCC).

TABLE 2

| Strain reference | Bacteria | DNA batch |
|---|---|---|
| E-64028 | *L. brevis* | 0011111LBRE-DH |
| E-79105 | *Pectinatus cerevisiiphilus* | 0010212LPEC-DH |
| E-052900 | *L. backii* | 0011111LBAC-DH |
| E-991161 | *L. lindneri* | 0011111LLIN-DH |
| E-91459T | *Pediococcus damnosus* | 0011111PEDD-DH |
| E-79111T | *Megasphaera cerevisiae* | 0011011MEGC-DH |
| E-95503T | *L. frigidus* | 0011111LFRI-DH |
| DSM 15814 | *L. rossiae* | 0011111LRO-DH |
| E-011808 | *L. casei* | 0011111LCAS-DH |
| E-991162 | *L. collinoides* | 0011111LCOL-DH |
| E-991163 | *L. coryniformis* | 0011111LCOR-DH |
| E-89345 | *L. perolens* | 0011111LPER-DH |
| E-71034 | *L. plantarum* | 0011111LPLA-DH |

An *L. casei* assay kit (including a forward primer (SEQ ID NO: 28), a reverse primer (SEQ ID NO: 29), and a probe (SEQ ID NO: 30)) is used to test samples of DNA from each the 13 different bacteria of Table 2 according to the procedures of Example 1. All probes are labeled with 6-FAM fluorescent dye at 5' and BHQ1 quencher at 3' or ROX fluorescent dye at 5' and BHQ2 quencher at 3'.

The *L. casei* assay (SEQ ID NOs: 28-30) quantitatively detects *L. casei* target DNA at 10, 1,000 and 100,000 copies per PCR well. However, there is no positive signal in the presence of 100,000 copies of each of the other 12 bacteria of Table 2. Accordingly, the *L. casei* assay (SEQ ID NOs: 28-30) is highly specific for *L. casei*.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar references in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nucleic acid consisting of:
   (i) nucleotide sequence selected from the group consisting of SEQ ID NOs: 28-30; and
   (ii) a fluorescent label attached to the nucleic acid.

2. A collection of nucleic acids comprising:
   (i) a first nucleic acid consisting of the nucleotide sequence of SEQ ID NO: 28,
   (ii) a second nucleic acid consisting of the nucleotide sequence of SEQ ID NO: 29, and
   (iii) a third nucleic acid consisting of (a) the nucleotide sequence of SEQ ID NO: 30 and (b) a fluorescent label attached to the third nucleic acid.

3. An assay kit comprising the collection of nucleic acids according to claim 2.

4. A support comprising the collection of nucleic acids according to claim 2 immobilized on the support, wherein the support comprises at least one cartridge having a plurality of reaction chambers and a reservoir, the reaction chambers being connected to the reservoir via channels, at least one heating plate having at least two distinct zones that can be heated to at least two different temperatures; and means for relative displacement between said cartridge and said plate, allowing a cyclic variation of the temperature of the reaction chambers.

5. A method of hybridizing a collection of nucleic acids with nucleic acid of *Lactobacillus casei* in a foodstuff, the method comprising:
  (a) obtaining at least one test sample comprising *Lactobacillus casei* nucleic acid isolated from foodstuff; and
  (b) contacting the collection of nucleic acids immobilized on the support according to claim 4 with the at least one test sample under conditions allowing for the collection of nucleic acids to hybridize to the *Lactobacillus casei* nucleic acid.

6. The method according to claim 5, wherein the foodstuff is a beverage.

7. The method according to claim 5, wherein the foodstuff is beer.

* * * * *

SEQUENCE LISTING

<160> NUMBER OF SEQ ID NOS: 45

<210> SEQ ID NO 1
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1
acgaacgcat cccgttaaa                                                  19

<210> SEQ ID NO 2
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 2
ggaccagttc gccactcatc c                                               21

<210> SEQ ID NO 3
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 3
caagtgcttg cacggatttt aacattg                                         27

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
cttgcaaatc gttctttggg                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 5
tagcggtacg actgtcttgg                                                 20

<210> SEQ ID NO 6
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 6
tcaaacccta acctcagctc cagc                                            24

<210> SEQ ID NO 7
<211> LENGTH: 21
<212> TYPE: DNA
<213> ORGANISM: Artificial Sequence

```
<220> FEATURE:
<223> OTHER INFORMATION: Synthetic Sequence

<400> SEQUENCE: 7
tccaagtcga acgcacagat a                                              21

<210> SEQ ID NO 8
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 8
gggaaatgtt atcccccact ttt                                            23

<210> SEQ ID NO 9
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 9
agtggcggac gggtgagtaa cacg                                           24

<210> SEQ ID NO 10
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 10
aacgagcttc cgttgaatga c                                              21

<210> SEQ ID NO 11
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 11
cggcctgctt ctgggcaga                                                 19

<210> SEQ ID NO 12
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 12
tgcttgcact gatttcaaca atgaagc                                        27

<210> SEQ ID NO 13
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 13
tcaagttctg ttgcagggga                                                20
```

```
<210> SEQ ID NO 14
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 14
accggacaac gcttgccg                                                        18

<210> SEQ ID NO 15
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 15
tgaatgacgg taccctgtta gaaagcc                                              27

<210> SEQ ID NO 16
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 16
cgtcgaacga ggtctcctaa c                                                    21

<210> SEQ ID NO 17
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 17
gccttccagg tgttatcccc tt                                                   22

<210> SEQ ID NO 18
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 18
agtggcgaac tggtgagtaa cacgt                                                25

<210> SEQ ID NO 19
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 19
cgcgtgacgg taccgtaag                                                       19

<210> SEQ ID NO 20
<211> LENGTH: 21
<212> TYPE: DNA
<213> ORGANISM: Artificial Sequence
<220> FEATURE:
<223> OTHER INFORMATION: Synthetic Sequence
```

<400> SEQUENCE: 20
ggagccccgc acttttaaga c                                              21

<210> SEQ ID NO 21
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 21
taccgtaaga gaaagccacg gctaa                                          25

<210> SEQ ID NO 22
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 22
cgtagagatg cttgcatcga a                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 23
ggcttgcacg gatagatgat t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 24
ccaaccatgc ggttcatttt a                                              21

<210> SEQ ID NO 25
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 25
ccaaaccatg cggtttactt ta                                             22

<210> SEQ ID NO 26
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 26
ccaaccatgc ggttttcttt a                                              21

<210> SEQ ID NO 27

```
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 27
agtggcgaac gggtgagtaa cacg                                          24

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 28
tggcttgcac tgagattcga                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 29
ccaccatgcg gttcttggat                                               20

<210> SEQ ID NO 30
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 30
agtggcggac gggtgagtaa cacg                                          24

<210> SEQ ID NO 31
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 31
caacgcactg acgtcgacc                                                19

<210> SEQ ID NO 32
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 32
agccaaaggc cgtcttttac att                                           23

<210> SEQ ID NO 33
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 33
```

```
agtggcggac gggtgagtaa cacg                                      24

<210> SEQ ID NO 34
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 34
cctgttgagt gcttgcattt aactg                                     25

<210> SEQ ID NO 35
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 35
ggccaagtgt tatcccctac ttcaa                                     25

<210> SEQ ID NO 36
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 36
agtggcgaac tggtgagtaa cacgt                                     25

<210> SEQ ID NO 37
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 37
ccaggtgctt gcatcacca                                            19

<210> SEQ ID NO 38
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 38
tttccaaatg ttatcccctg ctg                                       23

<210> SEQ ID NO 39
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 39
agtggcggac gggtgagtaa cacg                                      24

<210> SEQ ID NO 40
<211> LENGTH: 22
<212> TYPE: DNA
```

```
<213> ORGANISM: Artificial Sequence
<220> FEATURE:
<223> OTHER INFORMATION: Synthetic Sequence

<400> SEQUENCE: 40
tgaagtcgaa cgaactctgg ta                                              22

<210> SEQ ID NO 41
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 41
gcccgaagcc atctttcaaa ctc                                             23

<210> SEQ ID NO 42
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 42
agtggcgaac tggtgagtaa cacgt                                           25

<210> SEQ ID NO 43
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 43
acacggtgct tgcaccaga                                                  19

<210> SEQ ID NO 44
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 44
ggcaaatgtt atcccccact tta                                             23

<210> SEQ ID NO 45
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 45
agtggcgaac gggtgagtaa cacg                                            24
```